United States Patent [19]

Shechter et al.

[11] Patent Number: 5,338,759
[45] Date of Patent: Aug. 16, 1994

[54] VANADYL COMPLEXES OF HYDROXAMATE CHELATORS AND PHARMACEUTICAL COMPOSITIONS COMPRISING THEM

[75] Inventors: Yoram Shechter; Abraham Shanzer; Jacqueline Libman, all of Rehovot, Israel

[73] Assignee: Yeda Research and Development Co. Ltd., Rehovot, Israel

[21] Appl. No.: 70,384
[22] PCT Filed: Oct. 6, 1992
[86] PCT No.: PCT/EP92/02306
§ 371 Date: Jun. 7, 1993
§ 102(e) Date: Jun. 7, 1993
[87] PCT Pub. No.: WO93/07155
PCT Pub. Date: Apr. 15, 1993

[30] Foreign Application Priority Data

Oct. 7, 1991 [IL] Israel ......................................... 99666

[51] Int. Cl.$^5$ .......................... A61K 31/28; C07F 9/00
[52] U.S. Cl. .................................... 514/492; 514/866; 556/42
[58] Field of Search ................... 556/42; 514/492, 866

[56] References Cited

U.S. PATENT DOCUMENTS

| 4,882,171 | 11/1989 | Posner et al. | 424/616 |
| 5,023,358 | 6/1991 | Clapiers et al. | 556/42 |
| 5,101,066 | 3/1992 | Shanzer et al. | 560/169 |

FOREIGN PATENT DOCUMENTS 0305264  3/1987  European Pat. Off. .

OTHER PUBLICATIONS

Y. Tor et al.; "Biomimetic Ferric Ion Carriers, Chiral Ferrichrome Analogues"; pp. 6518–6219; Journal of the American Chemical Society, vol. 109, (1987).

*Primary Examiner*—José G. Dees
*Assistant Examiner*—Porfirio Nazario
*Attorney, Agent, or Firm*—Browdy and Neimark

[57] ABSTRACT

Vanadyl complexes of chelating dihydroxamate compounds suitable for oral treatment of diabetes are disclosed. The dipodal hydroxamate ion carriers effectively bind and transport vanadyl ions across lipid membranes and potentiate glucose metabolism. The complexes may be generated in vivo by administration of a vanadyl salt and the hydroxamate ion carrier.

15 Claims, 5 Drawing Sheets

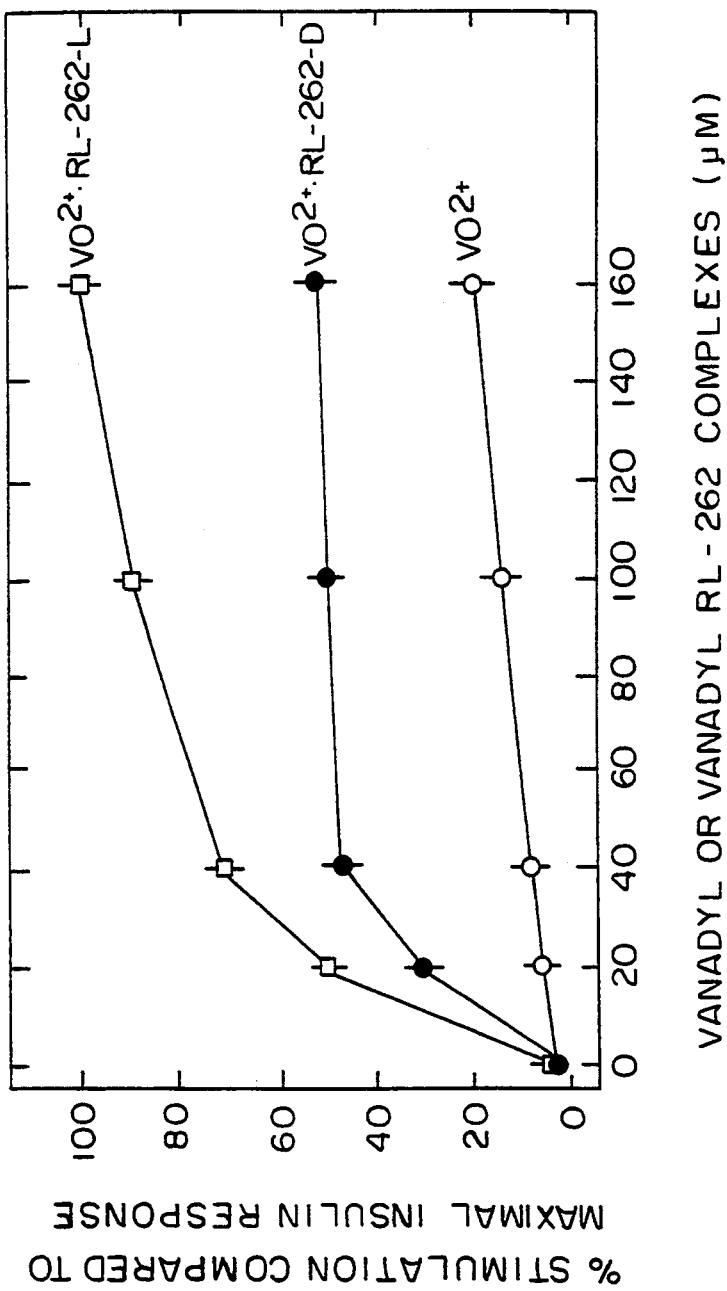

VANADYL COMPLEXES OF HYDROXAMATE CHELATORS AND PHARMACEUTICAL COMPOSITIONS COMPRISING THEM

FIELD AND BACKGROUND OF THE INVENTION

The present invention relates to vanadyl complexes useful for the treatment of diabetes.

Insulin-dependent diabetes mellitus is mainly treated with insulin. Since oral administration of insulin in mammals is ineffective, diabetic patients need to receive insulin by subcutaneous injection. The availability of orally active insulin substitutes is of great importance in the treatment of diabetes.

Vanadate ions ($VO_3-$, oxidation state +5) and also vanadyl ions ($VO^{2+}$, oxidation state +4) were shown to mimic nearly all of the various actions attributed to insulin in a large variety of in vitro (cellular) systems (Shechter, Y. (1990) Diabetes 39, 1–5) and thus, may be considered as wide-range insulin-mimicking agents. When administered orally (in drinking water) to streptozotocin-treated hyperglycemic rats, vanadate ions reduced the high levels of circulating glucose down to normal values and ameliorated many of the aberrations induced by hyperglycemia, including cardiac performance (Heyliger, C. E. et al (1985) Science 227, 1474–1476). In addition, disorders not directly related to hyperglycemia were also partially cured by oral vanadate therapy in this diabetic experimental model (Rossetti, L. and Laughlin, M. R. (1989) J. Clin. Invest. 84, 892–899). Vanadate therapy is also effective in experimental models of non-insulin dependent diabetes mellitus (NIDDM). In db/db and ob/ob mice, oral vanadate therapy induces long and persistent states of normoglycemia, while subcutaneous injections of insulin fail to do so (Meyerovitch, J. et al. (1991) J. Clin. Invest. 87, 1286–1294).

Japanese Patent Application published under No. 2292217 describes vanadium complexes, such as vanadium tartrate, for curing diabetes. U.S. Pat. No. 4,882,171 describes insulin mimic compositions containing a vanadate salt and a peroxide to treat diabetes mellitus. European Patent Application EP 305264 describes vanadyl complexes of cysteine and cysteine derivatives and compositions comprising them for oral treatment of insulin-dependent diabetes. McNeill, J. H. et al (J. Med. Chem. (1992) 35:1489–1491) have described a vanadyl complex of maltol (3-hydroxy-2-methyl-4-pyrone) shown to mimic insulin and to reduce plasma glucose values in rats.

Vanadium salts are thus seriously considered for therapy of human diabetes. Although vanadate has been found to be up to 4-5 fold more effective in vitro than vanadyl in mimicking insulin, probably due to its improved permeability across biological membranes, it has the disadvantage of being 6-10 times more toxic than vanadyl Waters, M. D. (1977) Adv. Med. Toxicol. 2, 147-189; Ramanadham S. et al. (1989) Metabolism 38, 1022-1028). Vanadyl, however, shows low cell permeability. Identifying means to enhance permeability of the less toxic vanadyl at low vanadyl concentrations would therefore open new possibilities for vanadium-based treatment of diabetes.

SUMMARY OF THE INVENTION

The present invention provides novel vanadyl ion ($VO^{2+}$) complexes of a chelating compound of general formula I:

$$R^2R^3C\{CH_2O(CH_2)_mCO[NHCHR(CH_2)_qCO]_n\text{-}NOHR^1\}_2 \quad (I)$$

wherein m is 1 or 2; q is 0, 1 or 2; n is 0 or 1; R, $R^1$, $R^2$ and $R^3$ independently designate each hydrogen, aryl, aralkyl, or alkyl optionally substituted by X, wherein X is OH, $OR^4$, $OCOR^4$, SH, SR, SCOR, COOH, $COOR^4$, $CONH_2$, $CONHR^4$, $CONR^4R^5$, $NH_2$, $NHR^4$, $NR^4R^5$ or $NHCOR^4$, where $R^4$ and $R^5$ are alkyl, and one of $R^2$ or $R^3$ may further designate X.

Some of the compounds of formula (I) are the subject of the U.S. Pat. No. 5,101,066 where they are described as tetradentate ligands suitable for the selective extraction of metal ions, such as $Cu^{2+}$ or $Zn^{2+}$, from a solution containing a plurality of cations.

It has now been found according to the present invention that the ion carriers of formula I effectively bind and transport vanadyl ions across lipid membranes and potentiate glucose metabolism. The structure of these carriers relies on a dipodal topology which allows a modular assembly of the binders, which in turn allows systematic modifications until optimal performance is achieved.

This is a novel family of vanadyl ion carriers possessing $C_2$-symmetry and utilizing two hydroxamate groups as ion binding sites, optionally having asymmetric carbons. Binding efficiencies and hydrophobicities are regulated by the use of a modular assembly. The effectiveness of the carriers depends on the position of their ion binding cavity, on their hydrophobicity and their chiral sense, the hydrophobic derivatives and L-amino acid derivatives being the more potent agents.

When applied together with vanadyl ions, the chelators of formula (I) exhibit a potentiating effect in stimulating glucose metabolism in rat adipocytes.

The invention further provides a pharmaceutical composition comprising as active ingredient a vanadyl complex of a compound of formula I, in particular for oral treatment of diabetes.

DESCRIPTION OF THE DRAWINGS

FIG. 5 shows the differential synergistic effects of enantiomeric-vanadyl carriers on $VO^{2+}$-dependent stimulation of lipogenesis. Lipogenesis (1 h; 37° C.) was carried out at increasing concentrations of $VO^{2+}$ (empty circles), $VO^{2+}$.RL-262-L, (empty squares) or $VO^{2+}$.RL-262-D (filled circles) complexes. The complexes (molar ratio 1:1.0) were prepared as described in Example 2.

DETAILED DESCRIPTION OF THE INVENTION

Figure 1A:
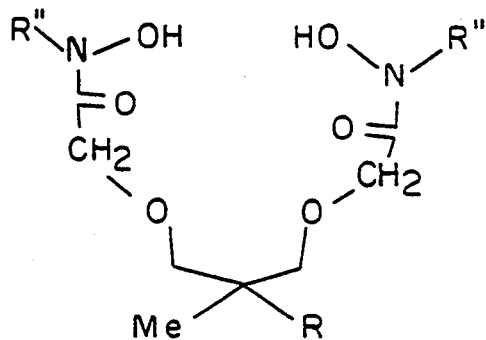
FIGS. 1a-1d show a schematic representation of the dihydroxamate ion carriers without FIG. 1a) and with amino acid bridges FIG. 1b and of the corresponding dipodal vanadyl ion complexes without (FIG. 1c) and with amino acid bridges (FIG. 1d).
Figure 1B:
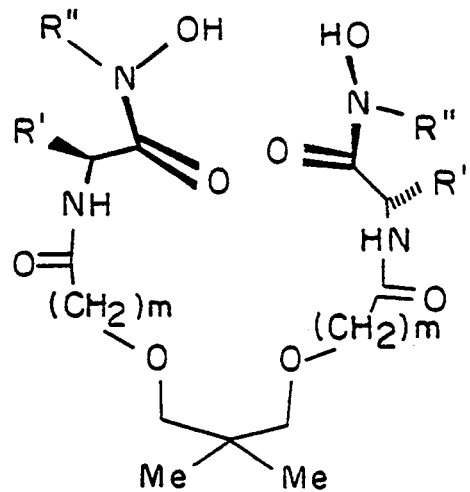
Figure 1C:
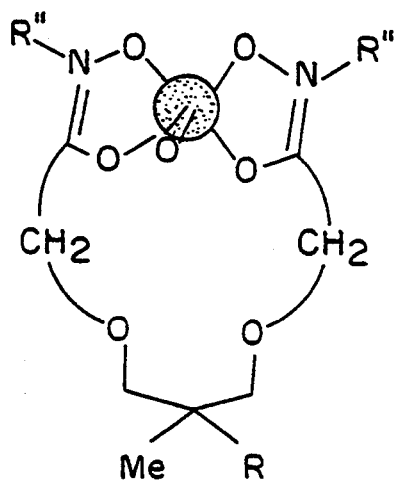
Figure 1D:
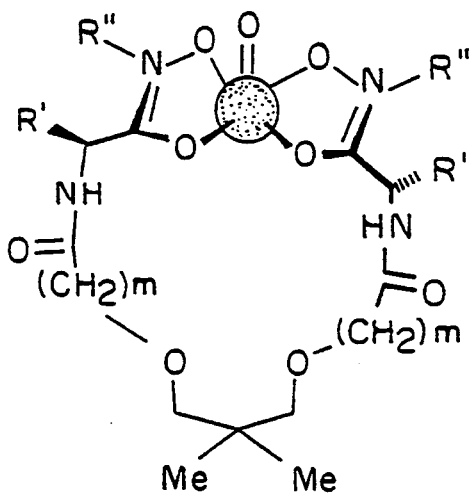

The superiority of the hydrophobic chelators relative to the hydrophilic ones together with the low molar ratio of chelator to $VO^{2+}$ to achieve maximal effect, indicate that these chelators act as vanadyl ionophores, as confirmed by carrier facilitated extraction of $VO^{2+}$ from water into chloroform with several chelators of formula (I). The effectiveness of these chelators goes down to 100:1 vanadyl: carrier ratios. Thus very low (micromolar) concentrations of the lipophilic ionophores are sufficient to maximally potentiate the effect of vanadyl ions on glucose metabolism.

The chelators potentiating effect is related to facilitated transport of $VO^{2+}$ ions across cellular membranes into the cells' interiors. The potency of vanadate ions was not increased by the chelators, although vanadate ions were effectively extracted from water into chloroform with the chelators. This is in line with earlier findings, that vanadyl ions, rather than vanadate ions, are the activating principle, and indicates that the effectiveness of vanadate is dependent on the cells' capability to reduce it to vanadyl ions. Vanadyl ions, on the other hand, do not require intracellular reduction events. Their limited solubility at neutral pH values and low permeability is now fully overcome by the ionophores applied here, which facilitate their permeation at low concentrations of the cation.

The moieties R, $R^1$, $R^2$, $R^3$, $R^4$ and $R^5$ may be the same or different. In one embodiment, they are all lower alkyl. The term "alkyl" means a straight or branched alkyl group having 1-12 carbon atoms, preferably lower alkyl of 1-6 carbon atoms. The term "aryl" means a $C_6$-$C_{14}$ carbocyclic aryl group, e.g., phenyl, naphthyl, anthracenyl, unsubstituted or substituted by one or more halogen, nitro, hydroxy, alkyl or aryl groups. The term "aralkyl" means a radical comprising aryl and alkyl groups as defined herein.

The preferred compounds of formula (I) to be used according to the present invention are the compounds wherein m is 1 or 2, n is 0 or 1, q is 0, $R^1$, $R^2$ and $R^3$ are lower alkyl, preferably methyl, and R is such a radical that the moiety —NHCHRCO— is derived from an α-amino acid, such as alanine (R is methyl), leucine (R is isobutyl), or isoleucine (R is sec.butyl).

The most preferred compounds of the formula (I) used according to the invention are of the formula

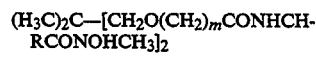

wherein R is isobutyl and m is 1 or 2.

The compounds of formula (I) are prepared according to the methods described in the U.S. Pat. No. 5,101,066. The vanadyl complexes are prepared by incubating a solution of a compound (I) in an organic solvent, e.g., a lower aliphatic saturated alcohol, with a water solution of a vanadyl salt. Any vanadyl salt which is water soluble may be used in the invention, the most preferred salt being vanadyl sulfate ($VOSO_4$).

The pharmaceutical compositions of the invention comprise an effective amount of a vanadyl complex of a compound of formula (I), optionally with a pharmaceutically acceptable carrier. They are useful both for insulin-dependent diabetes mellitus (IDDM) and for non-insulin-dependent diabetes mellitus (NIDDM).

Effective amounts of the complex are obtained by mixing the vanadyl salt and the chelator compound at a molar ratio of from 1:0.01 to 1.1, respectively. Very good synergistic effects are achieved at a molar ratio of 1:0.1. When used at equimolar ratio, an indicated dosage may be of 5-9 mg/kg, preferably 7-7.5 mg/kg, to be administered daily to a diabetic patient.

The compositions of the invention comprising the vanadyl complex, optionally with an antioxidant, e.g., ascorbic acid or α-tocopherol, are preferably administered orally, in capsules or tablets, or in a soluble form, such as suspension or drops. Slow release preparations of the preformed complex in coconut oil are also feasible.

The complex may be generated in vivo by administration of a vanadyl salt and a compound of formula I. The invention thus further comprises a pharmaceutical package comprising a pharmaceutical composition comprising a vanadyl salt, optionally with an antioxidant, e.g., ascorbic acid or α-tocopherol, and a pharmaceutical composition comprising a compound of formula I, with instructions how to administer them to the patient. The two ingredients may also be comprised each within a compartment of a single composition, e.g., a capsule, separated by a non-permeable membrane.

The compositions of the invention may be administered alone or in combined treatment with insulin, for treatment of insulin-sensitive patients.

The invention further relates to the use of vanadyl complexes of the compounds of formula (I) for the treatment, preferably oral, of diabetes. The complex may be generated in vivo by administration of a vanadyl salt , e.g. vanadyl sulfate and a compound of formula (I).

In another aspect, the invention relates to a method of treatment of diabetic patients which comprises the administration to said patients of an effective amount of a vanadyl complex of a compound of formula (I), or of effective amounts of a vanadyl salt and a compound of formula (I), alone or in combination with insulin therapy.

The invention will now be illustrated by the following non-limiting examples.

EXAMPLES

Example 1. Synthesis of the Chelators of Formula (I)

Several dipodal chelators of formula (I) were prepared according to the three-step method described in U.S. Pat. No. 5,101,066, and in Tor, Y. et al. (J. Amer. Chem. Soc. 109:6518–6519), involving:

(i) preparation of the biscarboxylates of the formula $R^2R^3C$—[$CH_2O(CH_2)_mCOOC_6Cl_5$]$_2$, starting from the parent alcohols $R^2R^3C(CH_2OH)_2$;

(ii) preparation of the hydroxyl amines or hydroxamates of the formula $H(NCHRCO)_nNOHR^1$, and (iii) coupling of the hydroxyl amines or hydroxamates with the bis-carboxylates, resulting in compounds of the formula:

$$R^2R^3C\text{—}[CH_2O(CH_2)_mCO(NHCHRCO)_N\text{-}NOHR^1]_2,$$

| Code | m | n | $R^2$ | $R^3$ | R | $R^1$ |
|---|---|---|---|---|---|---|
| RL-239 | 1 | 0 | Me | Me | — | Me |
| RL-280 | 1 | 0 | Me | Pr | — | Me |
| RL-282 | 1 | 0 | Me | Me | — | $CH_2CH_2COOEt$ |
| RL-262 | 1 | 1 | Me | Me | iBu | Me |
| RL-261 | 1 | 1 | Me | Me | Me | Me |
| RL-252 | 2 | 1 | Me | Me | iBu | Me | wherein Me is methyl, Et is ethyl, Pr is propyl and iBu is isobutyl.

The tripodal trishydroxamate Et-C[$CH_2O(CH_2)$- $_2CONHCHiBuCONOHCH_3$]$_3$ was synthesized (as described in U.S. Pat. No. 4,966,997) and used as reference compound for comparison (code number 1367). All amino acid residues used were of the natural L-configuration except for RL-262, which was prepared from either L-leu or D-leu to provide enantiomeric carriers.

The chelators were found to extract vanadyl ions from aqueous into lipid media (chloroform), and to subsequently release the bound metal when treated with aqueous glutathione solutions. Extraction experiments were performed by equilibrating equal volumes of 1 mM vanadyl sulfate in 1N aqueous $H_2SO_4$ with 1 mM chelator in chloroform for 3 days. Then the two phases were separated and the organic phases equilibrated with equal volumes of 10 mM glutathione in 0.1N aqueous $H_2SO_4$. Similarly, 1 mM sodium vanadate in 1N aqueous $H_2SO_4$ was equilibrated overnight with an equal volume of 1 mM chelator RL-252 in chloroform. The phases were then separated and the organic layer equilibrated with an equal volume of 10 mM glutathione in 01.N aqueous $H_2SO_4$. Vanadium contents of the aqueous layers were determined by inductive-coupled plasma atomic absorption (Perkin-Elmer 5500).

The results are summarized in Table I. As seen from the data, the extraction efficacies of the chelators for vanadyl salts decrease in the order 262>252>1367>261. Under analogous conditions, RL-252 was found to extract 31% vanadate from water into chloroform, and to release 81% of the bound ion, when treated with aqueous glutathione.

TABLE I

Extraction efficiencies and potencies of the various chelators in augmenting vanadyl-dependent stimulation of lipogenesis

| Chelator designation[a] | % of V extracted[b] | % of V released[c] | Concentration to produce half-maximal potentiation μM | Relative potentiation ability % |
|---|---|---|---|---|
| RL-252 | 17 | 29 | 1.50 ± 0.05 | 100 |
| RL-262 | 18.4 | 49 | 1.60 ± 0.05 | 90 |
| RL-262(D) | | | 3.50 ± 0.1 | 43 |
| RL-261 | 9.0 | <2 | 8.33 ± 0.4 | 18 |
| RL-239 | | | 4.17 ± 0.1 | 36 |
| RL-280 | | | 5.00 ± 0.2 | 30 |
| RL-282 | | | 25.0 ± 1.5 | |
| #1367 | 10.0 | 40 | 2.63 ± 0.1 | 57 |

[a] All amino acid residues used were of L-configuration, unless otherwise stated.
[b] % of $VO^{2+}$ extracted from water into chloroform.
[c] % of $VO^{2+}$ released from complex in chloroform into water.

Example 2. Preparation of the Vanadyl Complexes

Vanadyl-chelator complexes were prepared in plastic tubes by mixing $VOSO_4$ (500 nmoles) and 5 to 500 nmoles of the various chelators dissolved in ethanol, for 2–5 hours at 22° C. and at pH 4.5. Glutathione may be optionally added to create a reducing environment.

The complexes were characterized by ESR-spectrometry or spectrophotometrically after oxidation to vanadate. The ESR values for the vanadyl complex are of RL261: $A_{\parallel} = 183$ G; $g_{\parallel} = 1.98$; $g_{\perp} \sim 2.0$. The electronic spectrum for a representative vanadate complex is: $\lambda_{max} = 440$ nm ($\epsilon 2290$) in aqueous methanol, pH=3.2.

Example 3. Effect of Vanadate and Vanadyl in Stimulating Lipogenesis in Rat Adipocytes Rat adipocytes were prepared essentially by the method of Rodbell (Rodbell, M. (1964) J. Biol.Chem. 239, 375–380). The fat pads of three male Wistar rats were cut into small pieces with scissors and suspended in 3 ml of Krebs-Ringer Bicarbonate (KRB) buffer containing NaCl, 110 mM; $NaHCO_3$, 25 mM; KCl, 5 mM; $KH_2PO_4$, 1.2 mM; $CaCl_2$, 1.3 mM and $MgSO_4$, 1.3 mM, and 0.7% BSA (pH 7.4). The digestion was performed with collagenase (type 1, 134 units/mg, Worthington: 1 mg/ml) in a 25 ml flexible plastic bottle under an atmosphere of carbogen (95% $O_2$, 5% $CO_2$) for 40 min at 37° C. with vigorous shaking. Five ml of buffer was then added and the cells were passed through a mesh screen. The cells were then allowed to stand for several minutes in a 15 ml plastic test tube at room temperature, floating, and the buffer underneath was removed.

This procedure (suspension, floating and removal of buffer underneath) was repeated 3 times.

In the lipogenic assay, for measurement of glucose uptake and its incorporation into lipids (lipogenesis), the adipocyte suspensions (3×10² cells/ml) were divided into plastic vials (0.5 ml per vial) and incubated for 60 min at 37° C. under an atmosphere of 95% $O_2$, 5% $CO_2$ with 0.2 mM D-[U-$^{14}$C]glucose (4–7 mCi/mol, New England Nuclear), in either the presence or absence of insulin (100 ng/ml, Sigma), sodium-ortho-vanadate, vanadyl sulphate and vanadyl-chelator complexes (prepared as described in Example 2). No change in the pH value upon addition between 1 and 10 μl of either vanadyl or vanadyl-chelator complexes to the buffered cell suspensions was observed. Lipogenesis was terminated by adding toluene-based scintillation fluid (1.0 ml per vial) and the radioactivity in extracted lipids were counted (Moody, A. J. et al., (1974) Horm. Metab. Res. 6, 12-16). Control experiments were conducted with either ethanol alone (0.04-0.2%) or RL-252 (0.1-0.3 mM). In all experiments insulin-stimulated lipogenesis was 4- to 5-fold higher than basal. Vbasal~2,000 cpm per $3 \times 10^5$ cells/h; Vinsulin~8,000-10,000 cpm per $3 \times 10^5$ cells/h.

The results shown in tables and figures are presented as means ±SE. The number of experiments was between 3 and 7. The assays were performed in duplicate or triplicate.

Figure 2:
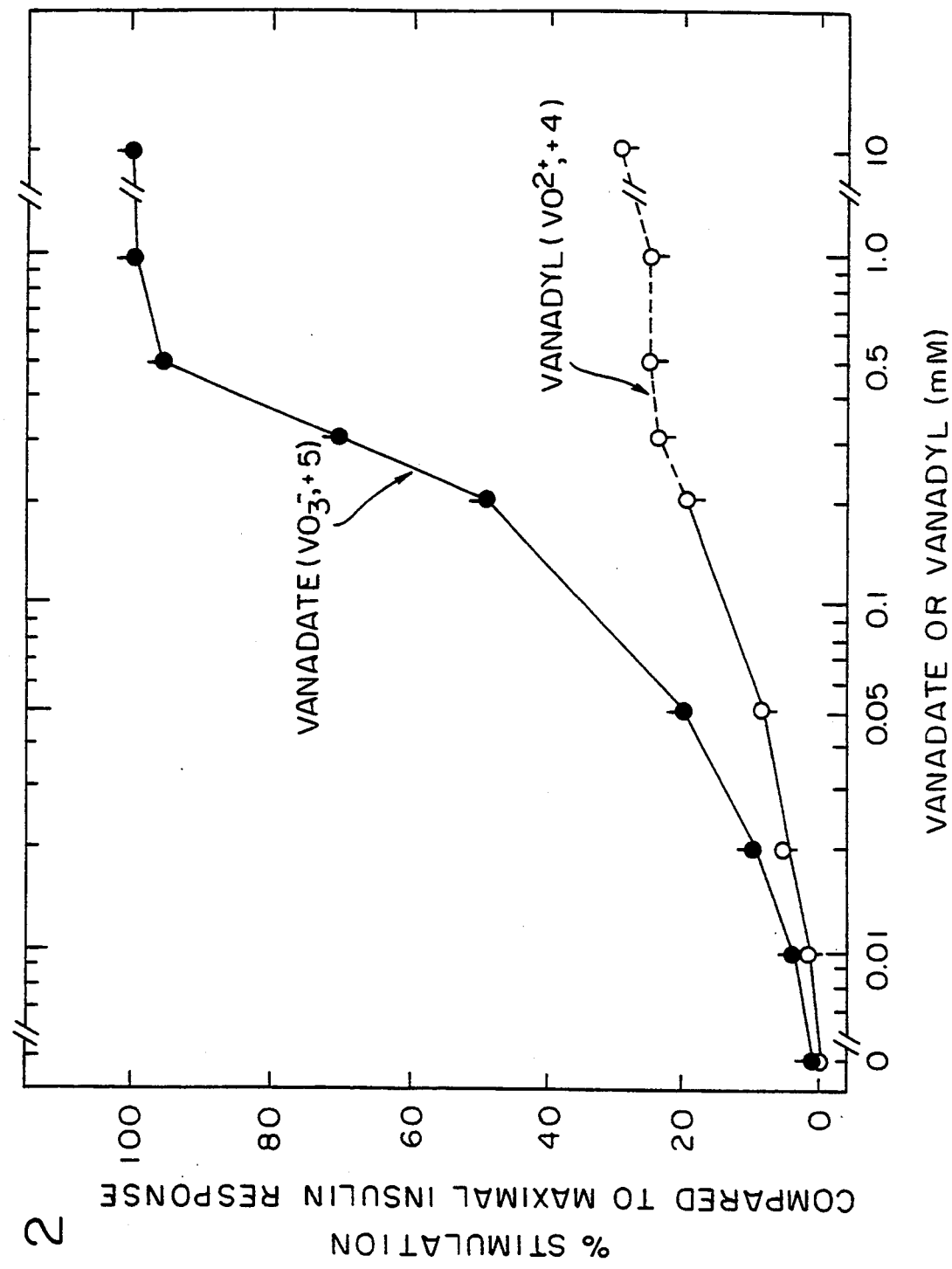
FIG. 2 illustrates the effects of increasing concentrations of vanadate or vanadyl on rates of lipogenesis. Lipogenesis was carried out for 1 h at 37° C. in vials containing about $1.5 \times 10^5$ cells suspended in Krebs-Ringer-Bicarbonate (KRB) buffer (0.7% BSA, pH 7.4), 0.2 mM [U-$^{14}$C]glucose and the indicated concentrations of vanadate (filled circles) or vanadyl (empty circles) ions. Results are expressed as percentages of stimulation compared to a maximal insulin response. The dashed line represents data collected at concentrations where vanadyl salts precipitate. The assay was run in duplicate.

Initially the dose response curve and extent of stimulation of lipogenesis by both vanadate and vanadyl were evaluated (FIG. 2). Vanadate stimulated lipogenesis to the same extent (100%) as insulin. The $ED_{50}$ value for vanadate amounted to 180±25 μM. Vanadyl also stimulated lipogenesis, but unlike vanadate, stimulation is incomplete and amounts to about 20-30% of the maximal effects of insulin or of vanadate (FIG. 2). The $ED_{50}$ value for vanadyl was calculated to be 100±20 μM in stimulating lipogenesis.

Example 4. Activity of Chelators (I) in Potentiating Vanadyl-Dependent Stimulation of Lipogenesis In the experiments summarized in FIG. 3, vanadyl sulfate was preincubated with equimolar concentrations of RL-252 (2-5 hours at room temperature) before addition to the cells, which were then assayed for lipogenesis. Under these conditions, the dose response curve was shifted to the left. Also, the extent of stimulation increased and even exceeded that of insulin itself. Thus, $ED_{50}$ values of $VO^{2+}$ alone or $VO^{2+}$.RL-252 complex were 100±20 and 30±4 [2M respectively, and the extent of stimulation was 25±3 and 115±5%, respectively. Altogether, the carriers increased the potency of $VO^{2+}$ in stimulating lipogenesis 7- to 10-fold in various experiments. Ethanol (0.2%) or RL-252 alone (0.1-0.3 mM) did not show any effect on basal or insulin-stimulated lipogenesis (Table II).

The potentiating actions of several related chelators on vanadyl-stimulated lipogenesis were studied (Table I). RL-262 and RL-252 were found to have the strongest potentiating effects. The order of reactivity was found to be RL-252≧RL-262>1367>RL-239>RL-280>RL-261>RL-282.

In contrast to the effect observed with vanadyl ions, RL-252 did not potentiate vanadate ($VO_{3-}$) stimulating glucose metabolism. This was true under several experimental conditions, namely at varying molar ratios of $VO_{3-}$ to RL-252 and at short or prolonged preincubating conditions. Thus, the potentiating effect of RL-252 is restricted to vanadyl ions (Table II).

TABLE II

Effect of RL-252 on $VO^{2+}$ and $VO_3^-$ stimulated lipogenesis in rat adipocytes[a]

| Additions | [U—$^{14}$C]glucose incorporated into lipids (cpm/3 × $10^5$ cells/h) | % of the maximal insulin response |
| --- | --- | --- |
| None | 2,300 ± 70 | 0 |
| Insulin 16.7 μM | 10,200 ± 100 | 100 |
| RL-252 200 μM | 2,340 ± 70 | 0 |
| RL-252 200 μM plus insulin 16.7 μM | 10,150 ± 100 | 100 |
| Vanadyl 60 μM | 3,500 ± 70 | 15 |
| Vanadyl 60 μM + RL-252 20 μM | 10,700 ± 120 | 106 |
| Vanadate 50 μM | 4,000 ± 50 | 21 |
| Vanadate 50 μM + RL-252 10 μM | 3,800 ± 70 | 19 |
| Vanadate 50 μM + RL-252 30 μM | 4,100 ± 70 | 23 |
| Vanadate 50 μM + RL-252 50 μM | 3,650 ± 40 | 17 |

Figure 3:
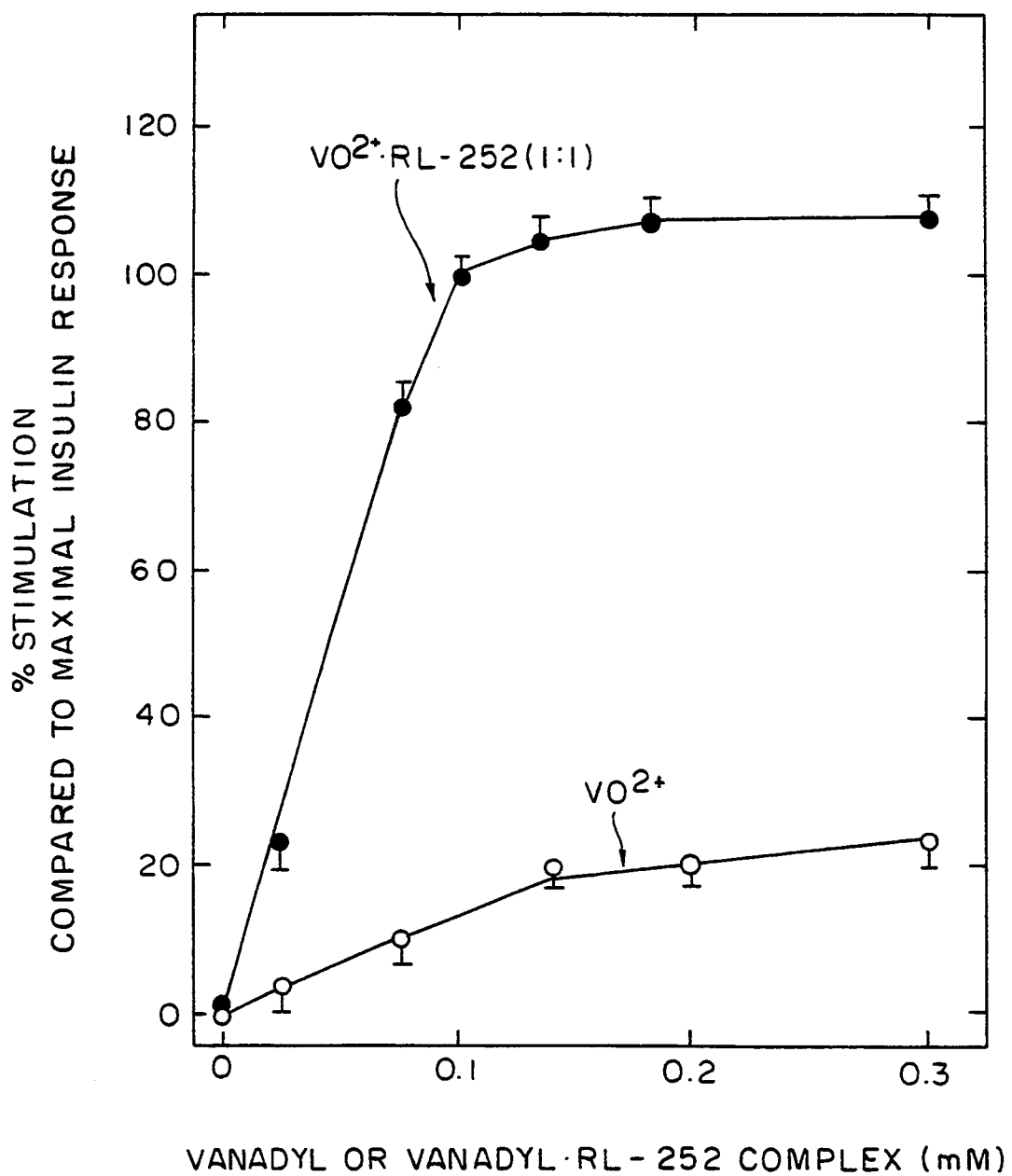
FIG. 3 illustrates the synergistic effect of chelator RL-252 on $VO^{2+}$-dependent stimulation of lipogenesis. Lipogenesis was carried out at pH 7.4 for 1 h at 37° C. under the experimental conditions described in the legend to FIG. 2, with the indicated concentrations of vanadyl ($VO^{2+}$, empty circles) or $VO^{2+}$.RL-252 complex (molar ratio=1:1, filled circles). RL-252 was preincubated with $VO^{2+}$ at pH 4.5 for 2 h at room temperature and aliquots (1-7.5 μl) were then added to adipocyte suspensions (0.5 ml each, in KRB buffer, pH 7.4). Control experiments revealed no pH change at the highest concentration of complex added here.

[a]Experimental details are as described in the legend to FIG. 3. Vanadyl and vanadate were preincubated with the ionophores for 2-5 hours at pH 4.5 before application to the cell.

Example 5. The Effective Molar Ratio of RL-252 to Vanadyl Ions

Figure 4:
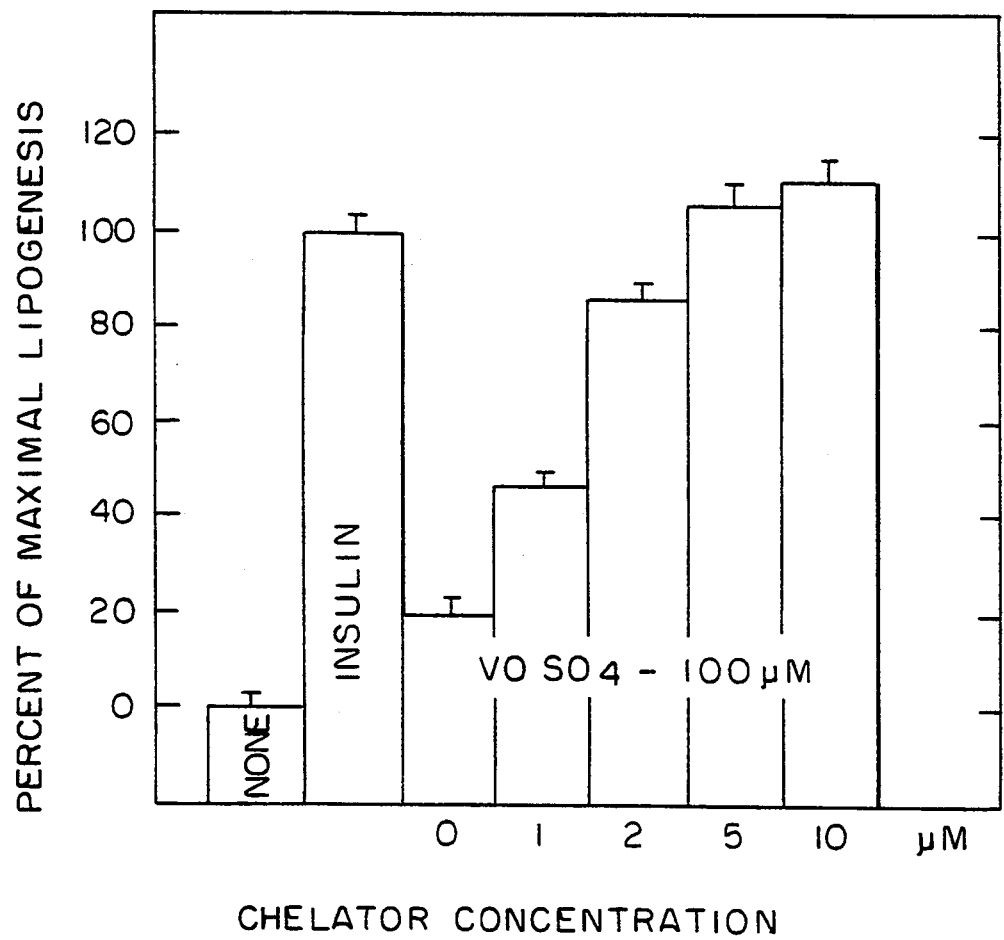
FIG. 4 illustrates the stimulation of lipogenesis at varying molar ratios of RL-252 to vanadyl ions. $VO^{2+}$.RL-252 complexes with different molar ratios were prepared by preincubating the increasing concentrations of the chelator with $VOSO_4$ as described in Example 2. Aliquots were then added to adipocyte suspension to achieve the indicated concentrations. Lipogenesis was carried out for 1 h at 37° C.

In the experiments summarized in FIG. 4, a constant concentration of $VOSO_4$ was preincubated with varying concentrations of RL-252 to obtain molar ratios of $VO^{2+}$ to RL-252 ranging from 1:0.01 to 1:0.1. Aliquots were then removed to evaluate their effect in stimulating glucose utilization in rat adipocytes. A potentiating effect was already observed at a molar ratio of 100:1 and the effect was maximal at a molar ratio of 10:1 of $VO^{2+}$ to RL-252, respectively (FIG. 4). Thus, very low concentrations of RL-252 already exhibit a maximal potentiating effect, indicating that RL-252 is operative in this system as a vanadyl ionophore.

Example 6. Activity of Enantiomeric Vanadyl Carriers. RL-262(L) versus RL-262(D)

The potentiating effects of the enantiomeric carriers, RL-262(L) assembled from L-Leu, and RL-262(D) assembled from D-Leu, were compared. As shown in FIG. 5 and in Table I, the effectiveness of the D-enantiomer is around 40% lower than that of the L-enantiomer. The pronounced lower effectiveness of the D-enantiomer suggests specific interactions of the vanadyl carrier complexes with biological recognition sites.

We claim:

1. A vanadyl complex of a compound of the general formula I:

$$R^2R^3C\{CH_2O(CH_2)_mCO[NHCHR(CH_2)_qCO]_n\text{-}NOHR^1\}_2 \qquad (I)$$

wherein m is 1 or 2; q is 0, 1 or 2; n is 0 or 1; R, $R^1$, $R^2$ and $R^3$ independently designate each hydrogen, aryl, aralkyl, or alkyl optionally substituted by X, wherein X is OH, $OR^4$, $OCOR^4$, SH, SR, SCOR, COOH, $COOR^4$, $CONH_2$, $CONHR^4$, $CONR^4R^5$, $NH_2$, $NHR^4$, $NR^4R^5$ or $NHCOR^4$, where $R^4$ and $R^5$ are alkyl, and one of $R^2$ or $R^3$ may further designate X.

2. A vanadyl complex according to claim 1 wherein in the compound of formula (I) m is 2, q is zero, n is 1, $R^1$, $R^2$ and $R^3$ are methyl and R is isobutyl.

3. A vanadyl complex according to claim 1 wherein in the compound of formula (I) m is 1, q is zero, n is 1, $R^1$, $R^2$ and $R^3$ are methyl and R is isobutyl.

4. A pharmaceutical composition for the treatment of diabetes comprising as active ingredient an effective amount of a vanadyl complex as claimed in claim 1, and a pharmaceutically acceptable carrier.

5. A pharmaceutical composition as claimed in claim 4 in a form suitable for oral administration.

6. A pharmaceutical composition as claimed in claim 4, further comprising an antioxidant.

7. A pharmaceutical composition according to claim 6, wherein said antioxidant comprises ascorbic acid or α-tocopherol.

8. A method for the oral treatment of diabetes which comprises orally administering to a diabetic patient an effective amount of a vanadyl complex of a compound of formula (I) as claimed in claim 1.

9. A method for the oral treatment of diabetes which comprises administering to a diabetic patient effective amounts of a vanadyl salt and a compound of the general formula (I):

wherein m is 1 or 2; q is 0, 1 or 2; n or 0 or 1; R, $R^1$, $R^2$ and $R^3$ independently designate each hydrogen, aryl, aralkyl, or alkyl optionally substituted by X, wherein X is OH, $OR^4$, $OCOR^4$, SH, SR, SCOR, COOH, $COOR^4$, $CONH_2$, $CONHR^4$, $CONR^4R^5$, $NH_2$, $NHR^4$, $NR^4R^5$ or $NHCOR^4$, where $R^4$ and $R^5$ are alkyl, and one of $R^2$ or $R^3$ may further designate X.

10. A method according to claim 8 wherein the treatment is combined with administration of insulin.

11. A pharmaceutical composition for the treatment of diabetes, comprising a vanadyl salt and a compound of the general formula (I):

wherein m is 1 or 2; q is 0, 1 or 2; n or 0 or 1; R, $R^1$, $R^2$ and $R^3$ independently designate each hydrogen, aryl, aralkyl, or alkyl optionally substituted by X, wherein X is OH, $OR^4$, $OCOR^4$, SH, SR, SCOR, COOH, $COOR^4$, $CONH_2$, $CONHR^4$, $CONR^4R^5$, $NH_2$, $NHR^4$, $NR^4R^5$ or $NHCOR^4$, where $R^4$ and $R^5$ are alkyl, and one of $R^2$ or $R^3$ may further designate X, wherein said vanadyl salt and said compound of formula (I) are separated from one another in the composition.

12. A pharmaceutical package having two compartments, a first compartment containing a vanadyl salt and a second compartment containing a compound of the general formula (I):

wherein m is 1 or 2; q is 0, 1 or 2; n or 0 or 1; R, $R^1$, $R^2$ and $R^3$ independently designate each hydrogen, aryl, aralkyl, or alkyl optionally substituted by X, wherein X is OH, $OR^4$, $OCOR^4$, SH, SR, SCOR, COOH, $COOR^4$, $CONH_2$, $CONHR^4$, $CONR^4R^5$, $NH_2$, $NHR^4$, $NR^4R^5$ or $NHCOR^4$, where $R^4$ and $R^5$ are alkyl, and one of $R^2$ or $R^3$ may further designate X.

13. A method for the oral treatment of diabetes which comprises orally administering to a diabetic patient an effective amount of a vanadyl complex of a compound of formula (I) as claimed in claim 2.

14. A method for the oral treatment of diabetes which comprises orally administering to a diabetic patient an effective amount of a vanadyl complex of a compound of formula (I) as claimed in claim 3.

15. A method according to claim 9, wherein the treatment is combined with administration of insulin.

* * * * *